(12) United States Patent
Clarke

(10) Patent No.: US 6,258,455 B1
(45) Date of Patent: Jul. 10, 2001

(54) ANTIMICROBIAL ULTRA-MICROFIBER CLOTH

(75) Inventor: George G. Clarke, Wilmette, IL (US)

(73) Assignee: Sweports Limited, Chicago, IL (US)

( * ) Notice: Subject to any disclaimer, the term of this patent is extended or adjusted under 35 U.S.C. 154(b) by 0 days.

(21) Appl. No.: 09/281,119

(22) Filed: Mar. 29, 1999

(51) Int. Cl.[7] .................................................. B32B 27/34
(52) U.S. Cl. ...................... 428/395; 428/907; 428/394; 428/392; 442/220; 442/239; 442/240
(58) Field of Search .................................. 428/364, 365, 428/280, 394, 233, 395, 905, 393, 907, 221, 392; 442/220, 239, 240

(56) References Cited

U.S. PATENT DOCUMENTS

| | | | |
|---|---|---|---|
| 3,699,958 | * 10/1972 | Szucs | 128/146.2 |
| 3,959,556 | * 5/1976 | Morrison | 428/364 |
| 4,343,853 | * 8/1982 | Morrison | 428/233 |
| 4,344,853 | 8/1982 | Morrison | 428/233 |
| 5,804,274 | 9/1998 | Nordin | 428/89 |
| 5,882,357 | * 3/1999 | Sun et al. | 8/189 |

* cited by examiner

*Primary Examiner*—Merrick Dixon
(74) *Attorney, Agent, or Firm*—Mayer, Brown & Platt

(57) ABSTRACT

An antimicrobial material having at least one yarn having fine fiber of 1.0 denier or less and at least one yarn having antimicrobial fiber that are engaged with each other, wherein the antimicrobial fibers impart an antimicrobial property to the entire material. In a preferred embodiment, the yarns of fine fiber and yarns of antimicrobial fiber are woven or knitted together. It is further preferred that the fine fiber be less than 0.3 denier, have a diameter of approximately 3 microns, and have a generally triangular cross-section with sharp edges, therefore allowing the fine fiber to substantially remove bacteria, fungi and other microbes from a surface. It is also preferred that the antimicrobial fibers comprise an acetate fiber spun together with polyester to give the antimicrobial fiber added strength.

32 Claims, 1 Drawing Sheet

ANTIMICROBIAL ULTRA-MICROFIBER CLOTH

FIELD OF INVENTION

This invention relates generally to cleaning cloths. More particularly, this invention relates to a woven or knitted cleaning cloth comprising antimicrobial fiber combined with ultra-microfiber, microfiber or microfilament.

BACKGROUND OF INVENTION

It is presently known to use various types of woven and knitted cloths for cleaning purposes. Usually these cloths are made of natural fibers such as cotton or wool, or blends of such natural fibers with nylon, rayon, polyester, and the like. However, these cloths have several drawbacks when used for cleaning purposes.

First, because the fibers contained in such cloths are relatively large, they are incapable of removing particles and microbes that are smaller than the fibers of the cloth. Thus, although the cloths are able to remove relatively large particles, a substantial amount of the smaller particles and microbes are merely spread around the surface desired to be cleaned without being removed. This results in an incomplete cleaning operation.

A further problem with present woven or knitted cleaning cloths is that such cloths do not contain antimicrobial characteristics. As used herein, the term "antimicrobial" is intended to include both anti-fungicidal and anti-bacterial characteristics. Without antimicrobial characteristics, the prior cloths allow bacteria and fungi to propagate within the cloth, thus leading to unsanitary conditions in the cloth and a shorter useful life of the cloth. In addition, reuse of the same cloth may spread such bacteria and fungi to other surfaces.

A recent advancement in fiber technology has been the advent of microfibers, microfilaments and so-called "ultra-microfibers," such as those sold by Olsson Cleaning Technology of Kristinehamn, Sweden. These fibers and filaments generally comprise polyamides and polyesters and are superior in many ways to traditional fibers due to their small size and structure. In particular, the ultra-microfibers are generally triangular in cross-section, have sharp edges, and have a diameter of approximately three microns. Because a bacterium typically has a diameter of two to five microns, the extremely small size and structure of the ultra-microfiber allows that fiber to get beneath the bacteria or other small microbes and particles that are smaller than the fiber, and substantially remove them from a surface. Additionally, to improve performance, the ultra-microfibers are usually mixed with polyester fibers in a 50/50 ratio in the case of woven material, and a 70/30 ratio of polyester to ultra-microfiber in the case of knitted material.

The cleaning properties of the ultra-microfibers are further enhanced because they have a cationic (positive) charge due to the presence of the polyamide in the ultra-microfibers. Most dirt and dust particles, bacteria, pollen, oxidation on metals, etc., have an anionic (negative) charge. Thus, the ultra-microfibers naturally attract negatively charged particles, bacteria, etc.

Besides the ultra-microfiber's ability to pick up small particles, the ultra-microfiber has superior absorption properties. This is because the ultra-microfiber's small diameter translates into a much larger surface area than that found in conventional fibers. The small diameter of the fibers also provides a particularly powerful capillary action, which, in addition to pulling in liquid, also pulls in particulates and microbes contained within the liquid. Thus, the combination of the increased surface area and capillary action gives the ultra-microfiber cloth the ability to absorb vast amounts of liquid many times its own weight.

The ultra-microfibers may be woven or knitted together to construct a cleaning material. The ultra-microfibers may first be woven or knitted in an un-split form using techniques known in the art. After the material is woven or knitted, such material is then subjected to a chemical and mechanical process that splits the ultra-microfiber into its component filaments. This is accomplished by using a combination of heat and alkali, as is also known in the art.

Unfortunately, like the woven and knitted cloths before it, the use of such ultra-microfiber materials allows for the propagation of microbes that are removed during cleaning operations. As stated earlier, the propagation of such microbes causes unsanitary conditions in the cloth and leads to a lessened useful life of the cloth. In addition, reuse of the same cloth may spread such microbes to other surfaces. Thus, there is currently a need for a cloth that can remove small particles and microbes from a surface, and at the same time keep the microbes from propagating throughout the cloth.

Other needs will become apparent upon consideration of the following detailed description taken in conjunction with the drawings.

SUMMARY OF THE PREFERRED EMBODIMENTS

In one form of the invention, the aforementioned needs are fulfilled by an antimicrobial material comprising at least one yarn comprising fine fiber of 1.0 denier or less and at least one yarn comprising antimicrobial fiber that are engaged with each other, wherein the antimicrobial fibers impart an antimicrobial property to the entire material. In a preferred embodiment, the yarns of fine fiber and yarns of antimicrobial fiber are woven or knitted together. It is further preferred that the fine fiber be less than 0.3 denier, have a diameter of approximately 3 microns, and have a generally triangular cross-section with sharp edges, therefore allowing the fine fiber to substantially remove bacteria, fungi and other microbes from a surface. It is also preferred that the antimicrobial fibers comprise an acetate fiber spun together with polyester to give the antimicrobial fiber added strength.

DETAILED DESCRIPTION OF THE PREFERRED EMBODIMENTS

Figure 1:
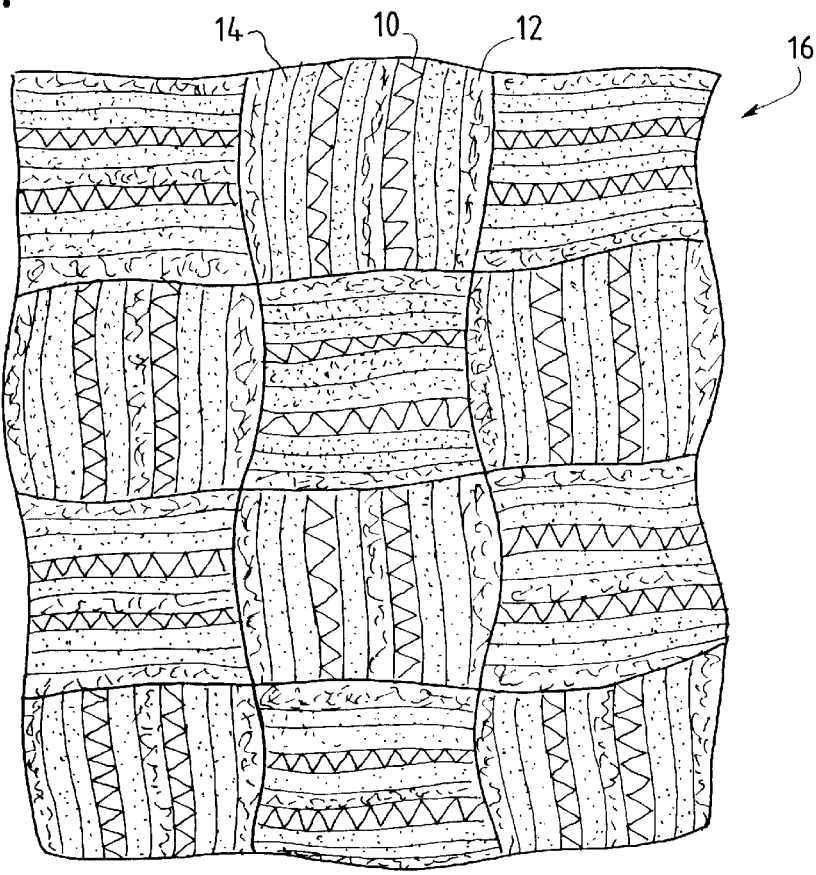
FIG. 1 shows a top plan view of a woven antimicrobial material.

While the present invention is capable of embodiments in various forms, there is shown in the drawings and will be hereinafter described a presently preferred embodiment with the understanding that the present disclosure is to be considered as an exemplification of the invention, and is not intended to limit the invention to the specific embodiment illustrated.

As stated above, the present invention relates to an ultra-microfiber material containing antimicrobial properties. Although the term "ultra-microfiber" is used herein, it should be understood that it is within the scope of the present invention that any other fine fiber can be used, such as microfibers and microfilaments. Typically, microfilaments are between 1.0 and 0.5 denier, microfibers are between 0.5 and 0.3 denier and ultra-microfibers are 0.3 denier or less.

The material of the present invention is produced by combining ultra-microfiber yarns as described above with yarns of antimicrobial fiber. Preferably, the antimicrobial fibers have an acetate base, such as the antimicrobial fiber sold under the name Microsafe® by Hoescht Celanese of South Carolina. The acetate fiber is a manufactured cellulosic fiber made from wood pulp and acetic acid. Because the fiber is cellulosic, it has characteristics of a natural fiber in that it is breathable and absorbent. However, one drawback to such a cellulosic fiber is that it lacks the proper strength characteristics for use in many types of cleaning operations.

Thus, to increase the strength of the acetate antimicrobial fibers, the fibers in the preferred embodiment are spun together with synthetic fibers such as rayon, nylon, or preferably, polyester. Usually, the acetate antimicrobial fibers are available in about 55 to about 150 denier weights, and it is preferable that the combination of polyester and antimicrobial fiber be in the range of about 250 to about 450 denier.

In order to impart antimicrobial properties to the acetate fiber, the fiber available from Hoescht Celanese of South Carolina contains an antimicrobial agent such as triclosan embedded within the interstices of the acetate fiber. This antimicrobial agent has been scientifically proven to inhibit the growth of a broad range of bacteria, mold, mildew and fungi. Because the antimicrobial agent is not water soluble, the antimicrobial agent will not wash out of the fibers. Furthermore, the antimicrobial protection is engineered to be durable and long lasting, so that the fiber can continuously provide antimicrobial protection throughout the life of a product.

The antimicrobial action of the fiber occurs as a result of the antimicrobial agent penetrating the wall of the bacteria and other thin-celled structures such as mold, mildew and fungi. When this penetration occurs, it prevents the thin-celled structures from functioning, developing and reproducing. Although the antimicrobial agent is able to destroy thin-walled organisms such as bacteria, it is safe for human contact due to the thick walls of animal cells. In fact, the antimicrobial agent has been shown to be considerably lower in toxicity than common products such as caffeine and aspirin.

Figure 2:
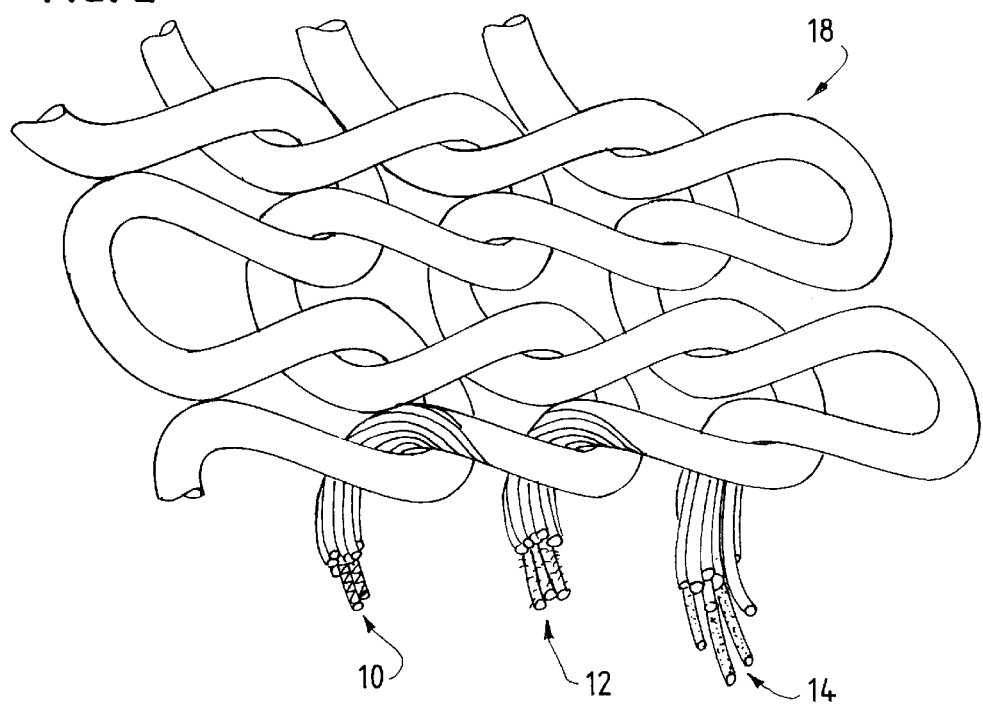
FIG. 2 shows a perspective view of a knitted antimicrobial material.

As stated above, the present invention is produced by combining the herein described antimicrobial fiber and ultra-microfiber. Now referring to FIGS. 1 and 2, it is preferable that the antimicrobial fiber and ultra-microfiber are first made into separate yarns (10 and 12, respectively) and then incorporated into the base 14 of a woven material (generally designated as reference numeral 16) or knitted material (generally designated as reference numeral 18 in FIG. 2), where the base material is preferably polyester. Furthermore, a singular yarn (not shown)comprising both antimicrobial fiber and ultra-microfiber can be combined into the base material of a woven or knitted material, or such yarn can be woven or knitted without such base material. Alternatively, the antimicrobial fibers and the ultra-microfibers can be intermixed by twisting two or more yarn ends, core spinning, air jet texturing, or the like (not shown). After the ultra-microfiber is combined with the other materials of the present invention, it is then subjected to the aforementioned heat and alkali process, which splits ultra-microfiber into its constituent filaments.

It is not necessary to use high concentrations of antimicrobial fiber to get the desired antimicrobial effect in the completed material of the present invention. Indeed, an antimicrobial fiber will create an effective zone of antimicrobial protection, thus imparting antimicrobial characteristics to other surrounding fibers, even if those surrounding fibers do not intrinsically have antimicrobial properties.

Thus, to produce the required antimicrobial properties in woven or knitted materials, it is preferable that approximately eighteen (18) percent of the total material comprise acetate antimicrobial fiber, while the rest of the material comprises ultra-microfibers or a combination of ultra-microfibers and other natural or synthetic fibers, such as polyester. It is presently known that a woven or knitted material comprising approximately eighteen (18) percent acetate antimicrobial fiber is effective at inhibiting the growth of both gram-positive and gram-negative bacteria. However, higher and lower concentrations of antimicrobial fiber may be acceptable in particular circumstances. It should be noted that the addition of dyes to the material of the present invention is known to have a detrimental effect on the antimicrobial properties of the antimicrobial fiber. Thus, in a preferred embodiment of the present invention, no dyes are used in the production of the material.

Furthermore, the concentration of ultra-microfiber to the antimicrobial fiber and the polyester fiber of the base material may vary depending on the particular application of the material. For example, where a woven or knitted material is used for a mop, a high concentration of ultra-microfibers makes movement of the mop difficult due to the high coefficient of friction between the fibers and the surface to be cleaned. This high coefficient of friction is caused by the small denier and diameter of the ultra-microfibers. Therefore, when the antimicrobial ultra-microfiber cloth is used in a mopping application, it is preferable to have a lower concentration of ultra-microfibers to reduce the friction of the material against the surface which is to be cleaned.

As will be apparent from the foregoing description, operation of the present invention is easily accomplished by wiping the antimicrobial ultra-microfiber cloth over a surface, in either a wet or dry state. As the cloth is wiped over a surface, the ultra-microfibers enable the cloth to remove substantially all of the particles on such surface, including very small particles and organisms such as bacteria, mold, fungi, etc., by getting beneath such particles and microbes. Furthermore, the cationic charge of the ultra-microfibers facilitates the removal of particles and microbes. If water is used in conjunction with the cleaning process, the capillary action of the ultra-microfibers also assists in drawing the particles into the cloth. Thus, after the cloth of the present invention is wiped over a surface, virtually no particles or microbes are left behind.

After the particles and microbes are removed from a surface, the antimicrobial fibers prevent the microbes from reproducing or growing. As stated earlier, the antimicrobial fiber creates an effective antimicrobial zone around the fiber, thus imparting antimicrobial properties to surrounding non-antimicrobial fibers, and that a cloth containing approximately eighteen (18) percent acetate antimicrobial fiber imparts an effective level of antimicrobial protection to the entire cloth.

It should be noted that it is within the scope of the present invention to provide a material that may be used for a multitude of purposes such as mops, dishcloths, towels, washing and wiping cloths, diapers, sanitary napkins and other feminine hygiene products, bed sheets, pillow cases and the like.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. An antimicrobial material comprising:
    at least one yarn comprising fine fiber of 1.0 denier or less; and
    at least one yarn comprising antimicrobial fiber engaged with said yarn comprising fine fiber.

2. The material of claim 1, wherein said material is woven.

3. The material of claim 1, wherein said material is knitted.

4. The material of claim 1, wherein said fine fiber is capable of removing microbes from a surface.

5. The material of claim 1, wherein said antimicrobial fiber comprises an acetate fiber spun together with a synthetic fiber, said antimicrobial fiber imparting an antimicrobial property to the entire material.

6. The material of claim 5, wherein said synthetic fiber is polyester.

7. The material of claim 1, wherein said fine fiber is less than 4 microns in diameter.

8. The material of claim 1, wherein said fine fiber comprises polyamide and imparts an overall cationic charge to said material.

9. The material of claim 1, wherein said fine fiber is 0.5 denier or less.

10. The material of claim 1, wherein said fine fiber is 0.3 denier or less.

11. The material of claim 1, wherein said antimicrobial fiber comprises at least eighteen percent of said material.

12. A cleaning cloth comprising:
    at least one yarn comprising fine fiber of 1.0 denier or less;
    at least one yarn comprising antimicrobial fiber engaged with said yarn of fine fiber, said antimicrobial fiber comprising an acetate fiber spun together with a synthetic fiber, wherein said antimicrobial fiber imparts an antimicrobial property to the entire cloth and said fine fibers are capable of removing microbes from a surface.

13. The cleaning cloth of claim 12, wherein said cleaning cloth is woven.

14. The cleaning cloth of claim 13, wherein said cleaning cloth is knitted.

15. The cleaning cloth of claim 12, wherein said synthetic fiber is polyester.

16. The cleaning cloth of claim 12, wherein said fine fiber is 0.5 denier or less.

17. The cleaning cloth of claim 12, wherein said fine fiber is 0.3 denier or less.

18. The cleaning cloth of claim 12, wherein said fine fiber has a diameter of less than 4 microns.

19. The cleaning cloth of claim 12, wherein said fine fiber comprises polyamide and impart a cationic charge to said cleaning cloth.

20. The cleaning cloth of claim 12, wherein said antimicrobial fiber comprises at least eighteen percent of said cleaning cloth.

21. An antimicrobial cleaning cloth comprising:
    at least one yarn comprising fine fiber of 0.3 denier or less;
    at least one yarn comprising antimicrobial fiber engaged with said yarn comprising fine fiber;
    wherein said fine fiber is capable of removing microbes from a surface, and said antimicrobial fibers impart an antimicrobial property to the entire cloth.

22. The cleaning cloth of claim 21, wherein said cleaning cloth is woven.

23. The cleaning cloth according to claim 21, wherein said cleaning cloth is knitted.

24. The cleaning cloth of claim 21, wherein said antimicrobial fiber comprises an acetate fiber spun together with polyester.

25. The cleaning cloth of claim 21, wherein said fine fiber is less than 4 microns in diameter.

26. The cleaning cloth of claim 21, wherein said fine fiber comprises polyamide and imparts a cationic charge to the entire cloth.

27. The cleaning cloth of claim 21, wherein said antimicrobial fiber further comprises the antimicrobial agent triclosan.

28. The cleaning cloth of claim 21, wherein said antimicrobial fiber comprises at least eighteen percent of said cleaning cloth.

29. An antimicrobial material comprising:
    at least one yarn comprising antimicrobial fiber and fine fiber of less than 1.0 denier.

30. The material of claim 29, wherein said material is woven.

31. The material of claim 29, wherein said material is knitted.

32. The material of claim 29, wherein said antimicrobial fiber comprises at least eighteen percent of said material.

* * * * *